United States Patent
Saadat (10) Patent No.: US 6,991,643 B2
(45) Date of Patent: Jan. 31, 2006

(54) MULTI-BARBED DEVICE FOR RETAINING TISSUE IN APPOSITION AND METHODS OF USE

(75) Inventor: Vahid Saadat, Saratoga, CA (US)

(73) Assignee: USGI Medical Inc., San Clemente, CA (US)

( * ) Notice: Subject to any disclaimer, the term of this patent is extended or adjusted under 35 U.S.C. 154(b) by 33 days.

(21) Appl. No.: 09/746,579

(22) Filed: Dec. 20, 2000

(65) Prior Publication Data

US 2002/0077661 A1 Jun. 20, 2002

(51) Int. Cl.
*A61B 17/11* (2006.01)

(52) U.S. Cl. ........................................ 606/221
(58) Field of Classification Search ............... 606/221, 606/213, 215, 151, 153; 602/41; 604/304; 2/908–920; 24/72.5, 442–447, DIG. 29
See application file for complete search history.

(56) References Cited

U.S. PATENT DOCUMENTS

| | | | |
|---|---|---|---|
| 3,166,072 A | * | 1/1965 | Sullivan, Jr. |
| 3,494,006 A | | 2/1970 | Brumilk |
| 3,874,388 A | | 4/1975 | King et al. |
| 4,259,959 A | * | 4/1981 | Walker |
| 4,414,720 A | | 11/1983 | Crooms |
| 4,589,416 A | * | 5/1986 | Green .................... 606/220 |
| 4,632,097 A | * | 12/1986 | Brooks ................... 602/16 |
| 4,816,339 A | | 3/1989 | Tu et al. |
| 5,013,316 A | | 5/1991 | Goble et al. |
| 5,081,714 A | * | 1/1992 | Liu .......................... 2/418 |
| 5,171,252 A | | 12/1992 | Friedland |
| 5,224,946 A | | 7/1993 | Hayhurst et al. |
| 5,236,445 A | | 8/1993 | Hayhurst et al. |
| 5,258,016 A | | 11/1993 | DiPoto et al. |
| 5,342,376 A | | 8/1994 | Ruff |
| 5,342,393 A | | 8/1994 | Stack |

(Continued)

FOREIGN PATENT DOCUMENTS

| | | | |
|---|---|---|---|
| WO | 90/09763 | * | 9/1990 |
| WO | WO 98/32401 | | 7/1998 |
| WO | WO 99/38454 | | 8/1999 |
| WO | WO 00/27292 | | 11/2000 |
| WO | WO 00/69365 | | 11/2000 |
| WO | WO 01/26557 | | 4/2001 |
| WO | WO 02/32345 A2 | | 10/2001 |
| WO | WO 01/85034 | | 11/2001 |
| WO | WO 01/89392 A3 | | 11/2001 |
| WO | WO 01/89392 A2 | | 11/2001 |
| WO | WO 03/090633 A2 | | 11/2003 |

OTHER PUBLICATIONS

US 6,447,535, 9/2002, Jacobs et al. (withdrawn)
Hayashi, K. et al. (1997). "The Effect of Thermal Heating on the Length and Histological Properties of the Glenohumeral Joint Capsule", *The American Journal of Sports Medicine*, 25(1):107–112.

(Continued)

*Primary Examiner*—Isamel Izaguirre
(74) *Attorney, Agent, or Firm*—Townsend and Townsend and Crew LLP (57) ABSTRACT

A multi-barbed apparatus is provided, and methods of use, for penetrating two sides of a wound and holding the edges in apposition. The apparatus may be inserted within a wound or underneath the skin, and mechanically adheres the two sides of the wound together. The apparatus includes a biocompatible substrate carrying a multiplicity of tissue penetrating barbs on a least one side thereof, and may be formed as a rigid or flexible sheet, tube or other shape.

46 Claims, 4 Drawing Sheets

U.S. PATENT DOCUMENTS

| | | |
|---|---|---|
| 5,354,298 A | 10/1994 | Lee et al. |
| 5,380,334 A | 1/1995 | Torrie et al. |
| 5,383,897 A * | 1/1995 | Wholey ............... 606/213 |
| 5,403,326 A | 4/1995 | Harrison et al. |
| 5,417,699 A | 5/1995 | Klein et al. |
| 5,423,856 A | 6/1995 | Green |
| 5,423,885 A * | 6/1995 | Williams ............... 623/1.17 |
| 5,458,609 A | 10/1995 | Gordon et al. |
| 5,462,561 A | 10/1995 | Voda |
| 5,480,403 A | 1/1996 | Lee et al. |
| 5,489,298 A | 2/1996 | Love et al. |
| 5,527,321 A | 6/1996 | Hinchliffe |
| 5,540,704 A | 7/1996 | Gordon et al. |
| 5,571,116 A | 11/1996 | Bolanos et al. |
| 5,584,859 A * | 12/1996 | Brotz |
| 5,601,558 A | 2/1997 | Torrie et al. |
| 5,639,276 A | 6/1997 | Weinstock et al. |
| 5,643,320 A | 7/1997 | Lower et al. |
| 5,667,513 A | 9/1997 | Torrie et al. |
| 5,683,417 A | 11/1997 | Cooper |
| 5,700,273 A | 12/1997 | Buelna et al. |
| 5,702,421 A | 12/1997 | Schneidt |
| 5,713,903 A | 2/1998 | Sander et al. |
| 5,720,753 A | 2/1998 | Sander et al. |
| 5,766,234 A | 6/1998 | Chen et al. |
| 5,779,719 A | 7/1998 | Klein et al. |
| 5,797,960 A | 8/1998 | Stevens et al. |
| 5,810,847 A | 9/1998 | Laufer et al. |
| 5,823,956 A | 10/1998 | Roth et al. |
| 5,829,447 A | 11/1998 | Stevens et al. |
| 5,836,955 A | 11/1998 | Buelna et al. |
| D404,128 S | 1/1999 | Huebner |
| 5,855,614 A | 1/1999 | Stevens et al. |
| 5,868,749 A | 2/1999 | Reed |
| 5,895,404 A | 4/1999 | Ruiz |
| 5,916,224 A * | 6/1999 | Esplin ............... 606/151 |
| 5,928,244 A | 7/1999 | Tovey et al. |
| 5,944,739 A | 8/1999 | Zlock et al. |
| 5,948,000 A | 9/1999 | Larsen et al. |
| 5,948,001 A | 9/1999 | Larsen |
| 5,957,916 A | 9/1999 | Jeevanandam et al. |
| 5,968,047 A | 10/1999 | Reed |
| 5,993,459 A | 11/1999 | Larsen et al. |
| 6,013,083 A | 1/2000 | Bennett |
| 6,036,690 A | 3/2000 | De La Plaza Fernandez |
| 6,068,648 A | 5/2000 | Cole et al. |
| 6,074,395 A | 6/2000 | Trott et al. |
| 6,079,414 A | 6/2000 | Roth |
| 6,086,591 A | 7/2000 | Bojarski |
| 6,146,387 A | 11/2000 | Trott et al. |
| 6,152,144 A | 11/2000 | Lesh |
| 6,165,183 A | 12/2000 | Kuehn et al. |
| 6,206,886 B1 | 3/2001 | Bennett |
| 6,231,561 B1 | 5/2001 | Frazier et al. |
| 6,245,079 B1 | 6/2001 | Nobles et al. |
| 6,269,819 B1 | 8/2001 | Oz et al. |
| 6,270,515 B1 * | 8/2001 | Linden et al. ............... 606/213 |
| 6,280,448 B1 | 8/2001 | Trott et al. |
| 6,290,674 B1 | 9/2001 | Roue et al. |
| 6,290,702 B1 | 9/2001 | Fucci et al. |
| 6,311,623 B1 | 11/2001 | Zaruba |
| 6,334,873 B1 | 1/2002 | Lane et al. |
| 6,346,074 B1 | 2/2002 | Roth |
| 6,346,109 B1 | 2/2002 | Fucci et al. |
| 6,355,030 B1 | 3/2002 | Aldrich et al. |
| 6,363,940 B1 | 4/2002 | Krag |
| 6,368,339 B1 | 4/2002 | Amplatz |
| 6,428,550 B1 * | 8/2002 | Vargas et al. ............... 606/153 |
| 6,485,503 B2 | 11/2002 | Jacobs et al. |
| 6,645,226 B1 | 11/2003 | Jacobs et al. |
| 2001/0044637 A1 | 11/2001 | Jacobs et al. |
| 2001/0051815 A1 | 12/2001 | Esplin |
| 2002/0022861 A1 | 2/2002 | Jacobs et al. |
| 2002/0035361 A1 | 3/2002 | Houser et al. |
| 2002/0042621 A1 | 4/2002 | Liddicoat et al. |
| 2002/0087048 A1 | 7/2002 | Brock et al. |
| 2002/0087049 A1 | 7/2002 | Brock et al. |
| 2002/0087166 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0183768 A1 | 12/2002 | Deem et al. |

OTHER PUBLICATIONS

Naseef III, G.S. et al. (1997). "The Thermal Properties of Bovine Joint Capsule, The Basic Science of Laser –and Radiofrequency–Induced Capsular Shrinkage", *The American Journal of Sports Medicine*, 25(5):670–674.

Selecky, M.T. et al. (1999). "The Effects of Laser–Induced Collagen Shortening on the Biomechanical Properties of the Inferior Glenohumeral Ligament Complex", *The American Journal of Sports Medicine* 27(2):168–172.

* cited by examiner

MULTI-BARBED DEVICE FOR RETAINING TISSUE IN APPOSITION AND METHODS OF USE

FIELD OF THE INVENTION

The present invention relates generally to multi-barbed devices for maintaining tissue in apposition to promote wound closure and healing or for attaching tissue to adjacent structures or organs, and methods of use of such devices.

BACKGROUND OF THE INVENTION

Several types of wound closure devices and methods are known, and typically include sutures, staples, surgical tapes and tissue adhesives. Application of most of these wound closure devices is time consuming, and requires considerable manual dexterity and patience. In addition, while these methods are functionally adequate, some may take too long to provide effective wound closure, or be cosmetically unappealing.

Most prevalent is the use of needles and sutures. Sutures provide high tensile strength, a low incidence of reopening, and can provide minimal cosmetic scarring. Application of sutures is by far the slowest method of obtaining wound closure, the sutures typically require removal and the use of anesthetic and have the highest tissue reactivity and application cost.

Surgical staples have the advantages of rapid application, low tissue reactivity, low cost, and reduced risk of needle-sticks (and hence transmission of blood borne disease) to the surgeon and attending staff. Staples generally have low tensile strength than sutures, generally must be removed, and may interfere with certain imaging modalities, such as MRI or CT scanning. In addition, because staples typically present smaller contact areas to the tissue being closed, they present a higher risk of the wound being torn open.

Surgical tapes provide the least tissue reactivity, rapid application, low infection rates and low cost, reduced risk of needle-sticks, and a high degree of patient comfort. Because such tapes are topically applied, they provide much lower tensile strength than sutures, and thus the highest incidence of inadvertent reopening. In addition, such tapes generally cannot be used in hairy body areas, and must be kept dry.

Tissue adhesives and sealants offer advantages of rapid application, low cost, and a high degree of patient comfort. In addition, such adhesives do not need to be removed. Drawbacks associated with tissue adhesives include low tensile strength and high incidence of wound reopening when applied in areas subject to high tensile loads.

Most biologically derived sealants adhere to tissue by participating in the normal clotting cascade. Fibrin glues, for example, are generally used to control bleeding or to reinforce suture or staple lines rather than to make tissues adhere, thus functioning more as hemostatic agents than glues. While several new technologies are under development that offer the potential for use in diffuse bleeding sites, fibrin glues generally are most effective in areas of inactive bleeding.

Drawbacks common to many previously known wound closure techniques, such as sutures and staples, typically involve the skin in one way or another and therefore cause disfigurement of the skin (i.e. the suture penetration points). In addition, because such devices only hold the tissue together at certain points, they do not take advantage of the entire tissue surface area to create a strong bond.

Drawbacks associated with tissue adhesives and sealants are that most of these glues take several minutes to set, may not work in a wet environments and provide only limited tensile strength. Such glues work by binding with individual molecules on either side of the wound and therefore recruiting a large surface area in the act of binding the two surfaces together. This is an improvement over the needle and suture method where discrete "points" or tracks defined by the puncture sites of the needle where the suture passes through or the puncture site of the staple have the role of providing support for the coaptation of the two surfaces.

In view of the foregoing, it would be desirable to provide wound closure devices and methods that merge the desirable features of previously known wound closure systems, i.e. to take advantage of the entire surface in coaptation as well as utilizing a mechanical element to retain the tissue portions in apposition.

It further would be desirable to provide wound closure devices and methods that allow a surgeon to close a wound rapidly and effectively without damaging the skin surface adjacent the wound, thus creating a scar.

It also would be desirable to provide wound closure devices and methods that provide a high-tensile strength bond and are not visible from outside the skin.

It still further would be desirable to provide wound closure devices and methods that may be used not only to establish and retain tissue portions in apposition, but which also may be used to provide adhesion to a large surface area, e.g., such as for hernia repair or attaching large skin grafts onto the surface of the body.

It also would be desirable to provide wound closure devices and methods wherein the devices may be configured in different shapes for different applications, including such shapes as a sheath, a cylinder, a ball a strip or a long rod like shape, and may be used intraoperatively or laparoscopically.

It yet further be desirable to provide wound closure devices and methods that can be used in wet or bleeding environments without significant loss of intended function.

It also would be desirable to provide wound closure devices that can be doped with a therapeutic agent, e.g., growth factor or thrombin, to aid wound healing or a clot enhancement.

SUMMARY OF THE INVENTION

In view of the foregoing, it is an object of the present invention to provide multi-barbed wound closure devices and methods for establishing and maintaining two sides of a wound in apposition.

It is another object of this invention to provide wound closure devices and methods that merge the desirable features of previously known wound closure systems, for example, by taking advantage of the entire surface in coaptation as well as utilizing a mechanical element to retain the tissue portions in apposition.

It is another object of the present invention to provide wound closure devices and methods that allow a surgeon to close a wound rapidly and effectively without damaging the skin surface adjacent the wound.

It also is an object of this invention to provide wound closure devices and methods that provide a high-tensile strength bond and are not visible from outside the skin.

It further is an object of the present invention to provide wound closure devices and methods that may be used not only to establish and retain tissue portions in apposition, but which also may be used to provide adhesion to a large surface area, e.g., such as for hernia repair or attaching large skin grafts onto the surface of the body.

It still further is an object of the present invention to provide wound closure devices and methods wherein the devices may be configured in different shapes for different applications, including such shapes as a sheath, a cylinder, a ball a strip or a long rod like shape, and may be used intraoperatively or laparoscopically.

It yet further is an object of the present invention to provide wound closure devices and methods that can be used in wet or bleeding environments without significant loss of intended function.

It also is an object of this invention to provide wound closure devices that can be doped with a therapeutic agent, e.g., growth factor or thrombin, to aid wound healing or a clot enhancement.

In accordance with the principles of the present invention, the wound closure device comprises a substrate having a plurality of biodegradable barbs extending from at least one surface of the substrate. The multi-barbed device therefore permits closure of a wound in a timely, cosmetic and convenient manner.

The substrate generally is in the form of a thin strip of bioabsorbable polymer, and may be solid or have perforations forming a mesh. Where provided, the perforations allow the tissue and body fluids to contact the other side and enhance the healing process.

Where designed for applications in bringing the tissue edges of a wound into apposition and maintaining the tissue in fixed relation during healing, the substrate is provided with a multiplicity of barbs projecting from opposing sides of the substrate. The barbs have a sharpened distal end to facilitate tissue penetration, and hooks that grasp the tissue penetrated. Alternatively, the multiplicity of barbs may project from only one side of the substrate, for example, where the device is to be used to mend large areas of tissue, e.g., in hernia repair.

In accordance with the methods of the present invention, the multi-barbed device of the present invention is inserted within a wound or underneath the skin, and mechanically attaches to and brings the opposing tissue sides together.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Referring to FIGS. 1 to 4, a preferred embodiment of multi-barbed, multi-sided device 20 of the present invention is described for attaching coapting and maintaining two sides of a wound. Device 20 comprises substrate 21 having multiplicity of barbs 22 projecting from opposite sides 23 and 24. Barbs 22 have sharpened distal ends 25 that enable the barbs to penetrate tissue.

Figures 1, 2, 3:
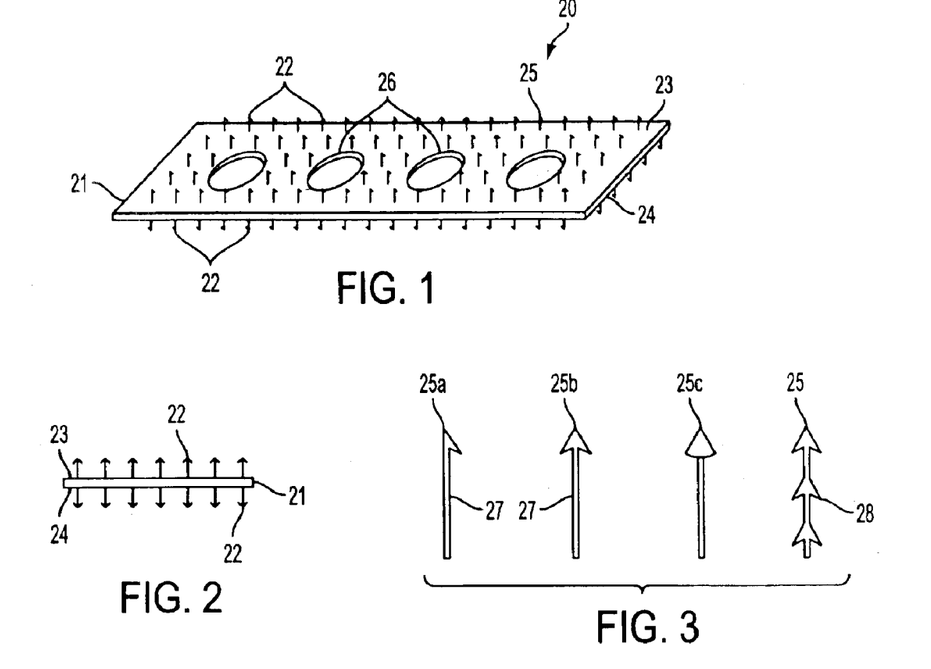
FIG. 1 is a perspective view of an illustrative wound closure device constructed in accordance with the principles of the present invention.
FIG. 2 is a side view of the device of FIG. 1.
FIG. 3 is a detailed view of various embodiments of barbs suitable for use with the device of the present invention.

Substrate 21 may be either rigid or flexible, and preferably comprises a thin sheet or strip of a bioabsorbable polymer that can be absorbed by the body such as polylactic acid, polyglycolic acid, polycaprolactone, polyethylene glycol, or other bioabsorbable polymers known in the art. Substrate 21 may by either solid or include mesh-like perforations 26 that permit the wound edges to communicate with one another, thereby facilitating the healing process. Depending upon the intended application, substrate 21 may be made sufficiently flexible to conform to the tissue to be joined.

In the embodiment of FIGS. 1–4, barbs 22 project substantially orthogonally away from the plane of substrate 21, and include distal tissue-piercing end 25 and shank 27. Barbs 22 preferably are dull enough to not penetrate a surgical glove yet sharp enough to penetrate tissue. Distal ends 25 of barbs 22 may have a harpoon configuration (25a in FIG. 3), an arrow configuration (25b in FIG. 3) or being conically shaped (25c in FIG. 3). In addition, barbs 22 may include additional ribs, hooks or projections 28 disposed along shanks 27 to further enhance the gripping ability of the barbs.

Barbs 22 preferably comprise a material that is sufficiently rigid to penetrate tissue during application, and is capable of withstanding the tensile forces expected during normal use, i.e., so the barbs cannot be pulled out and shanks 27 will not fracture in large numbers. Barbs 22 may comprise a bioabsorbable polymer, metal, or metal alloy. Barbs 22 may be made having shank lengths ranging from a fraction of a millimeter, e.g., for plastic surgery, to many millimeters, e.g., for large operations or veterinarian use.

Perforations 26 in device 20 reduce concerns that the substrate would be a barrier to healing, and instead allow the tissue edges and body fluids to contact one another across through substrate 21, thereby accelerating the healing process. The perforations are passageways for the tissue and body fluids to have free communication from one side to the other. Perforations 26 may comprise up 90% or more of the area of substrate 21.

In addition, substrate 21 and/or barbs 22 may be coated or impregnated with an anesthetic to reduce pain during wound healing. Alternatively, device 20 may include other drugs or therapeutic agents that provide some therapeutic effect during healing, for example, angiogenic agents or growth factors to facilitate wound healing, anti-inflammatory agents to reduce swelling or antibiotics to reduce infection.

Device 20, and the alternative embodiments described hereinafter, have a number of applications, including:

Routine surgical wound closure;
Orthopedic procedures such as meniscal repair;
Wartime field use for fast wound closure;
Plastic surgery where it is cosmetically desirable to avoid the use of sutures; and
Grafting a large piece of planar tissue, such as fascia or skin, onto an area of the body.

Still referring to device 20 to FIG. 1, device 20 preferably comprises a biodegradable polymer such as polyglycolic acid or polylactic acid, and is preferably flexible to conform to curved surfaces. Barbs 22 may be constructed of the same material or a different material and preferably also are bioabsorbable. The whole device 20, including substrate 21 and barbs 22, may be molded out of one of the foregoing polymers. Perforations 26 enable the two sides of the wound to communicate with one another to facilitate healing of the wound, as described above.

Figure 4:
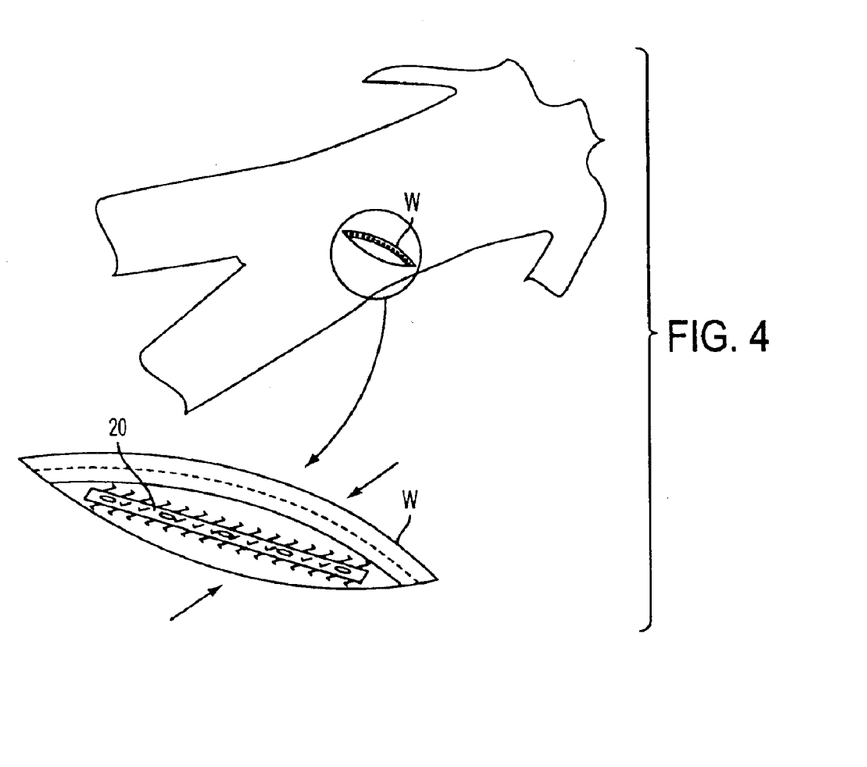
FIG. 4 is a perspective view of a preferred method of employing the device of FIG. 1 to close a wound in a human body.

In FIG. 4, device 20 is shown disposed within wound W. In accordance with a method of the present invention, device 29 is placed into the wound, and the two edges of the wound are approximated and squeezed together onto the multiplicity of barbs 22 so that tissue adhesion occurs. Barbs 22 thereby penetrate the tissue on both sides of substrate 21 and maintain the two edges of the wound firmly together.

Figure 5A:
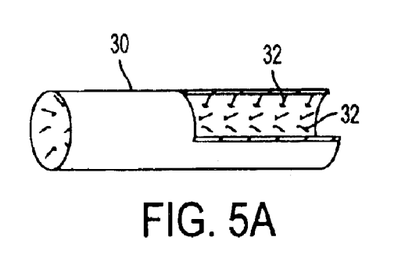
FIG. 5 is a perspective view, partly in section, of a tube constructed in accordance with the present invention.
Figure 5B:
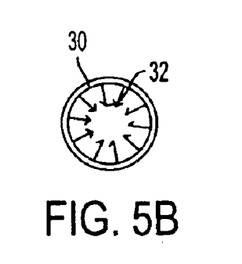

Referring now to FIGS. 5A and 5B, an alternative embodiment of the present invention in form of a tube is described. Tube 30, shown partly in section, includes a multiplicity of internal barbs 32 that project radially inward. The wall of tube 30 may comprise a solid material, such as a metallic or polymeric material, or may be in the form of a mesh.

Barbs 32 may be disposed only in regions adjacent to the ends of tube 30, or as shown in FIG. 5A, may extend for along the entire length of the interior of tube 30. Barbs 32 may project substantially orthogonally from the interior surface of tube 30, or may in addition be angled towards the mid-point of the tube.

In accordance with the methods of the present invention, if a blood vessel or a tendon is inserted into tube 30, it will be firmly engaged by the plurality of barbs 32, and will be unable to come back out of the tube. Thus, two ends of a torn tendon may be inserted into the tube 30 to provide a strong connection.

Figure 6:
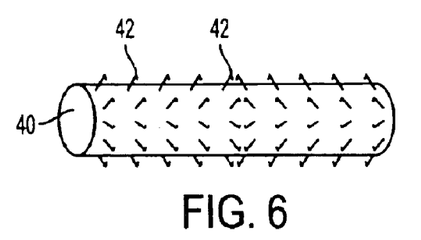
FIG. 6 is a perspective view of an alternative tube constructed in accordance with the present invention.

In FIG. 6, an alternative embodiment is depicted in which the multiplicity of barbs is disposed on the exterior of the tube. Tube 40 may have a solid or hollow cross-section, and may comprise either a rigid or flexible material. Barbs 42 allow a tubular structure, such as a vessel, to be pulled over tube 40 like a sock and be firmly gripped. Examples of applications include rejoining of a fallopian tube or vas deferens anastomosis to reverse sterilization in a female or male subject.

Figure 7:
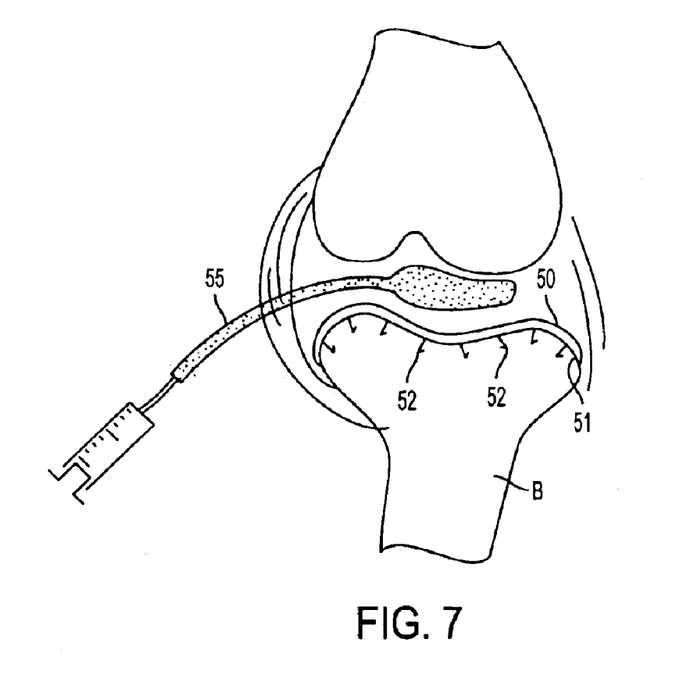
FIG. 7 is a view showing insertion of an artificial cartilage including the multi-barbed device of the present invention within a human knee.

In FIG. 7, an embodiment of the multi-barbed substrate of the present invention is described for use in joint repair to anchor artificial cartilage to the tibial chondyle. In this embodiment, artificial cartilage 50 is prepared having substrate 51 anchored to its lower surface. Substrate 51 includes multiplicity of barbs 52, as described hereinabove, projecting from substrate 51.

Artificial cartilage 50 is introduced arthroscopically in a contracted condition. Once disposed within in the knee space, artificial cartilage 50, including substrate 51, is unrolled over the tibial chondyle. High-pressure balloon 55, or some other mechanical means, e.g., a mallet, is then used to apply a force on the surface of the artificial cartilage and substrate, thereby forcing the multiplicity of barbs 52 into engagement with bone B.

Figure 8:
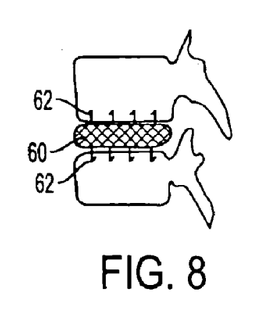
FIG. 8 is a view showing placement of an intervertebral disk including the multi-barbed device of the present invention within a human vertebrae.

Similarly, FIG. 8 depicts use of the structures and principles of the present invention for use in intervertebral disc replacement. Replacement disc 60 includes a multiplicity of barbs 62 on its upper and lower surfaces. Barbs 62 penetrate the vertebral end plate and stabilize it, thereby preventing rotation of the vertebrae and facilitating fusion. Replacement disc 60 preferably includes perforations, as described above, to aid in bone migration. Additionally, replacement disc 60 or barbs 62, or both, may be coated or impregnated with hydroxy apatite, as well as growth factors, to aid in the fusion process.

Figure 9:
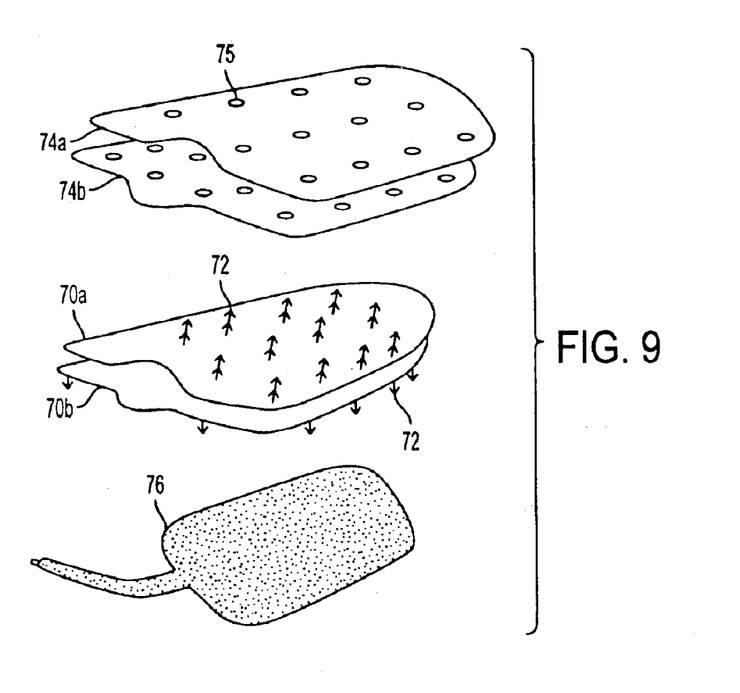
FIG. 9 is a perspective view of several components of the present invention in the form of a clamshell.

FIG. 9 depicts another embodiment of a device constructed in accordance with the present invention, in which the barbs of the device are shielded until it is desired to implant the device. Substrate halves 70a and 70b each carry a multiplicity of barbs 72. Substrate halves 70 are configured to be disposed within shield portions 74a and 74b. Shield portions 74a and 74b each include a multiplicity of openings 75 aligned with barbs 72. Balloon 76 is configured to be disposed between substrate halves 70a and 70b, so that upon application of an outward force by balloon 76, the barbs are driven through openings 75 in shield portions 74a and 74b and into the target tissue.

Figure 10A:
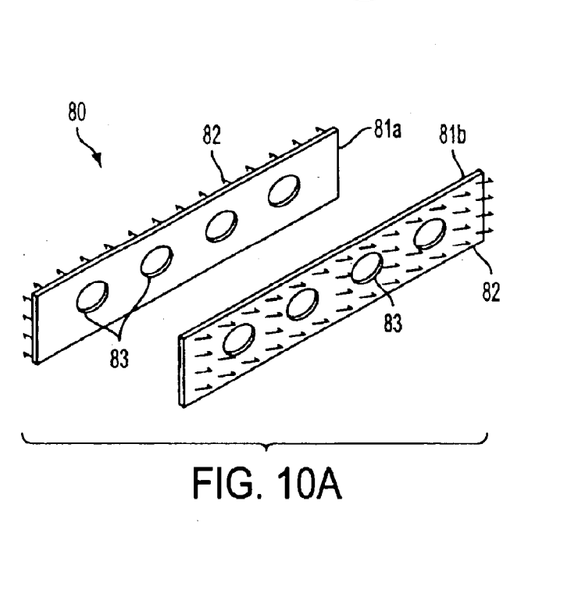
FIGS. 10A and 10B are, respectively, perspective and side views of the present invention in the form of two halves that are attachable by sutures.
Figure 10B:
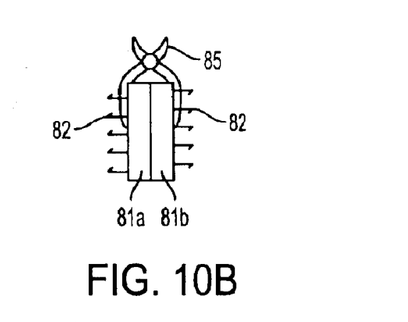

With respect to FIGS. 10A and 10B, another alternative embodiment is described. Device 80 includes substrate portions 81a and 81b, each carrying a multiplicity of barbs 82 as described above. Each of substrate halves 81a and 81b includes a plurality of suture eyelets 83. In accordance with the methods of the present invention, device 80 is employed by individually adhering the substrate halves 81a and 81b to the edges of the wound. A suture 85 is then threaded through eyelets 83 in substrate halves 81a and 81b, and the wound is closed by pulling the suture connecting the two halves to bring substrate halves 81a and 81b into apposition, as depicted in FIG. 10B. Suture 85 is then knotted, and any excess suture material removed.

Figure 11:
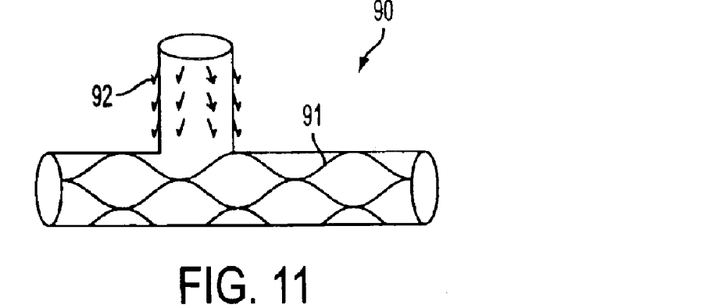
FIG. 11 is a side view of an anastomosis device including the multi-barbed device of the present invention suitable for use in coronary artery bypass grafting.

FIG. 11 depicts an embodiment of the present invention wherein stent-like structure 90 is used to side anastomose a blood vessel. Structure 90 includes non-barbed section 91 that is inserted into the parent vessel. Barbed portion 92 is then used to attach a bypass graft vessel.

Figure 12:
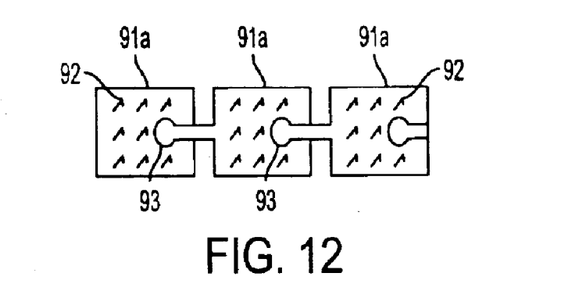
FIG. 12 is a side view of an embodiment of the present invention providing longitudinal flexibility.

FIG. 12 depicts yet another alternative embodiment of the wound closure device of the present invention. In this embodiment, substrate 91 comprises a rigid material including a multiplicity of barbs 92. To ensure that the substrate is capable of flexing, however, substrate 91 is divided into a series of jointed and interlinked units 91a, 91b and 91c. Joints 92 enable units 91a–91c to rotate relative to one another, thereby providing a degree of flexibility to the overall device.

Figure 13:
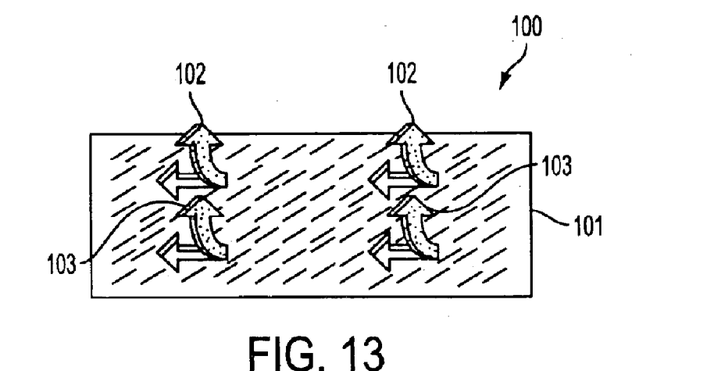
FIG. 13 is a perspective view of an alternative embodiment of the device of the present invention formed by stamping the barbs from the substrate material.

FIG. 13 depicts a method of manufacturing a multi-barbed device of the present invention. Device 100 comprises substrate 101 formed from a thin sheet of biocompatible polymer or metal alloy. Barbs 102 are die cut from substrate 101, and then bent out of the plane of substrate 101 to expose sharpened distal ends 103.

Figure 14:
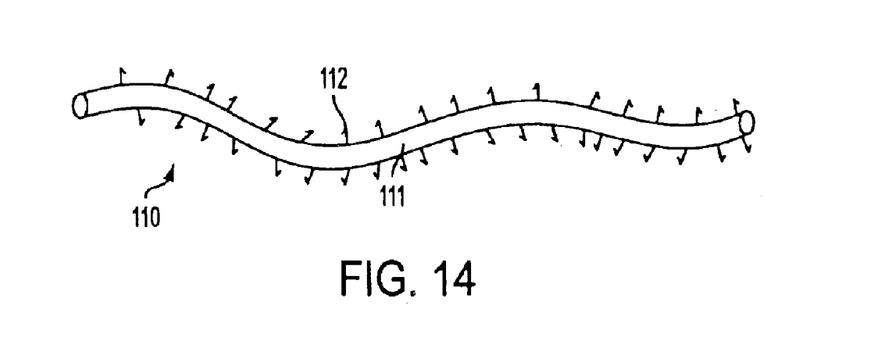
FIG. 14 is a side view of the alternative embodiment of the present invention in the form of a flexible rod coated with a plurality of the barbs.

FIG. 14 depicts an alternative embodiment to that shown in FIG. 6. Device 110, which may made available for dispensing in the form of a reel, comprises flexible substrate 111 carrying a multiplicity of barbs 112 on its exterior surface. Device 110 therefore may be unrolled and cut to length depending upon the specific desired application. For example, for non-medical industrial applications, in which it is desired to adhere two separate sheets together quickly, substrate 111 may comprise a strong plastic, e.g., Nylon, and the barbs 112 may comprise stainless steel or another metal alloy.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for closing a wound comprising:
    a first elongated substrate including first and second surfaces; and
    a second elongated substrate including first and second surfaces,
    wherein the second surfaces are configured to mate with each other,
    wherein the first surfaces are covered by a multiplicity of barbs configured to adhere for adhering to the wound.

2. The apparatus of claim 1, wherein the multiplicity of barbs projects from the first surface.

3. The apparatus of claim 2, wherein each elongated substrate further comprises portions defining a plurality of perforations that extend from the first surface to the second surface.

4. The apparatus of claim 3, wherein the plurality of perforations define suture eyelets.

5. The apparatus of claim 1, wherein each elongated substrate further comprises a coating of a therapeutic agent.

6. The apparatus of claim 1, wherein each elongated substrate is impregnated with a therapeutic agent.

7. The apparatus of claim 1 further comprising a therapeutic agent selected from a family of angiogenic growth factors.

8. The apparatus of claim 1, wherein the first and second surfaces are tied together using a suture.

9. The apparatus of claim 1, wherein each elongated substrate comprises a series of units interconnected by joints.

10. A method for performing an anastomosis comprising:
    providing a device comprising an elongated tubular substrate of a biocompatible material having a first surface coated or impregnated with a therapeutic agent, multiple rows of barbs projecting from the first surface;
    positioning the elongated substrate within a wound so that the multiplicity of barbs is directed towards the tissue defining a perimeter of the wound; and
    squeezing the perimeter of the wound against the multiplicity of barbs to adhere the perimeter of the wound to the elongated substrate.

11. The method of claim 10 further comprising, during wound healing, releasing a predetermined amount of the therapeutic agent into the vicinity of the wound.

12. A method for closing a tissue wound comprising:
    providing a device comprising first and second elongated substrate halves, each of the first and second elongated substrate halves comprising a biocompatible material having a first surface and a multiplicity of barbs projecting from the first surface;
    positioning the first elongated substrate half within a wound so that the multiplicity of barbs is directed towards the tissue defining a first portion of the perimeter of the wound;
    squeezing the first portion of the perimeter of the wound against the multiplicity of barbs to adhere the first portion of the perimeter of the wound to the first elongated substrate half;
    positioning the second elongated substrate half within the wound so that the multiplicity of barbs is directed towards the tissue defining a second portion of the perimeter of the wound; and
    squeezing the second portion of the perimeter of the wound against the multiplicity of barbs to adhere the second portion of the perimeter of the wound to the second elongated substrate half; and
    moving the first and second substrate halves into apposition.

13. The method of claim 12 wherein moving the first and second substrate halves into apposition comprises threading suture material through eyelets in the first and second elongated substrate halves and knotting the suture material.

14. Apparatus for closing a wound comprising:
    an elongated substrate comprising a biocompatible material, the elongated substrate having a first and a second surface, a plurality of perforations extending from the first surface and adapted to define suture eyelets; and
    multiple rows of barbs projecting from the first and second surfaces, wherein the multiple rows of barbs have having tissue-penetrating distal ends;
    a plurality of perforations extending from the first surface and adapted to define suture eyelets; and
    suture extending through at least one of the plurality of perforations.

15. The apparatus of claim 14, wherein the elongated substrate further comprises a coating of a therapeutic agent.

16. The apparatus of claim 14, wherein the elongated substrate is impregnated with a therapeutic agent.

17. The apparatus of claim 14, wherein each barb includes a shank coupling the tissue-penetrating distal end to the substrate, and one or more projections from the shank.

18. The apparatus of claim 17, wherein each barb is cut from the substrate.

19. The apparatus of claim 14, wherein the elongated substrate has the form of a tube.

20. The apparatus of claim 19, wherein the tube includes an interior lumen formed by the first surface.

21. The apparatus of claim 19, wherein the tube includes an exterior surface forming the first surface.

22. The apparatus of claim 14 further comprising a stent-like structure, wherein the elongated substrate forms a side anastomosis site of the apparatus.

23. The apparatus of claim 14, wherein the elongated substrate comprises a series of units interconnected by joints.

24. The apparatus of claim 14 further comprising a region of artificial cartilage coupled to the elongated substrate.

25. The apparatus of claim 14 further comprising a replacement intervertebral disc coupled to the elongated substrate.

26. Apparatus for closing a wound comprising:

an elongated substrate comprising a biocompatible material and impregnated with a therapeutic agent, the elongated substrate having a first surface; and multiple rows of barbs projecting from the first surface, the multiple rows of barbs having tissue-penetrating distal ends, wherein the elongated substrate has the form of a tube comprising an interior lumen formed by the first surface.

27. The apparatus of claim 26, wherein the elongated substrate further comprises a coating of the therapeutic agent.

28. The apparatus of claim 26, wherein each barb includes a shank coupling the tissue-penetrating distal end to the substrate, and one or more projections from the shank.

29. The apparatus of claim 28, wherein each barb is cut from the substrate.

30. The apparatus of claim 26 further comprising a stent-like structure, wherein the elongated substrate forms a side anastomosis site of the apparatus.

31. Apparatus for closing a wound comprising:

an elongated substrate comprising a biocompatible material and impregnated with a therapeutic agent, the elongated substrate having a first surface; and multiple rows of barbs projecting from the first surface, the multiple rows of barbs having tissue-penetrating distal ends, wherein the elongated substrate has the form of a tube comprising an exterior surface formed by the first surface.

32. The apparatus of claim 31, wherein the elongated substrate further comprises a coating of the therapeutic agent.

33. The apparatus of claim 31, wherein each barb includes a shank coupling the tissue-penetrating distal end to the substrate, and one or more projections from the shank.

34. The apparatus of claim 33, wherein each barb is cut from the substrate.

35. The apparatus of claim 31 further comprising a stent-like structure, wherein the elongated substrate forms a side anastomosis site of the apparatus.

36. Apparatus for repairing cartilage comprising:

an elongated substrate comprising a biocompatible material, the elongated substrate having a first surface, a multiplicity of barbs projecting from the first surface, the multiplicity of barbs having tissue-penetrating distal ends; and a region of artificial cartilage coupled to the elongated substrate.

37. The apparatus of claim 36, wherein the elongated substrate further comprises a coating of a therapeutic agent.

38. The apparatus of claim 36, wherein the elongated substrate is impregnated with a therapeutic agent.

39. The apparatus of claim 36, wherein each one of the multiplicity of barbs includes a shank coupling the tissue-penetrating distal end to the substrate, and one or more projections from the shank.

40. The apparatus of claim 39, wherein the multiplicity of barbs are cut from the substrate.

41. Apparatus for repairing an intervertebral disc comprising:

an elongated substrate comprising a biocompatible material, the elongated substrate having a first surface, a multiplicity of barbs projecting from the first surface, the multiplicity of barbs having tissue-penetrating distal ends; and a replacement intervertebral disc coupled to the elongated substrate.

42. The apparatus of claim 41, wherein the elongated substrate further comprises a coating of a therapeutic agent.

43. The apparatus of claim 41, wherein the elongated substrate is impregnated with a therapeutic agent.

44. The apparatus of claim 41, wherein each one of the multiplicity of barbs includes a shank coupling the tissue-penetrating distal end to the substrate, and one or more projections from the shank.

45. The apparatus of claim 44, wherein the multiplicity of barbs are cut from the substrate.

46. The apparatus of claim 41 further comprising a region of artificial cartilage coupled to the elongated substrate.

* * * * *